US012636440B2

(12) United States Patent
Helmer

(10) Patent No.: US 12,636,440 B2
(45) Date of Patent: May 26, 2026

(54) SENSOR DEVICE FOR ATTACHMENT TO AN INJECTION DEVICE

(71) Applicant: Sanofi, Paris (FR)

(72) Inventor: Michael Helmer, Frankfurt am Main (DE)

(73) Assignee: SANOFI, Paris (FR)

( * ) Notice: Subject to any disclaimer, the term of this patent is extended or adjusted under 35 U.S.C. 154(b) by 106 days.

(21) Appl. No.: 18/309,919

(22) Filed: May 1, 2023

(65) Prior Publication Data

US 2023/0285683 A1     Sep. 14, 2023

Related U.S. Application Data

(63) Continuation of application No. 16/957,330, filed as application No. PCT/EP2018/086100 on Dec. 20, 2018, now Pat. No. 11,672,916.

(30) Foreign Application Priority Data

Dec. 28, 2017     (EP) ..................................... 17306950

(51) Int. Cl.
A61M 5/315          (2006.01)
A61M 5/20           (2006.01)
(Continued)

(52) U.S. Cl.
CPC .......... A61M 5/31573 (2013.01); A61M 5/20 (2013.01); A61M 5/3204 (2013.01);
(Continued)

(58) Field of Classification Search
CPC .. A61M 5/31573; A61M 5/20; A61M 5/3204; A61M 2205/18;
(Continued)

(56) References Cited

U.S. PATENT DOCUMENTS 9,186,465  B2     11/2015   Jørgensen et al.
11,197,963  B2     12/2021   Helmer et al.
(Continued)

FOREIGN PATENT DOCUMENTS

CN          102300597          12/2011
CN          104902944          9/2015
(Continued)

OTHER PUBLICATIONS

International Preliminary Report on Patentability in International Appln. No. PCT/EP2018/086100, dated Jun. 30, 2020, 9 pages.
(Continued)

*Primary Examiner* — Lauren P Farrar
(74) *Attorney, Agent, or Firm* — Bond Schoeneck & King PLLC

(57) ABSTRACT

A supplementary device configured to be releasably attached to a distal end of a drug delivery device. The supplementary device comprising primary electronics, a non-contact acceleration sensor and a low power processor. The non-contact acceleration sensor is directed towards a proximal end of the drug delivery device and the low power processor is configured to: receive the signals output from the non-contact acceleration sensor; determine based on the signals that an outer needle cap of the drug delivery device has been removed; and in response to determining that an outer needle cap of the drug delivery device has been removed, send a wake-up signal to the primary electronics of the supplementary device.

23 Claims, 5 Drawing Sheets

(51) Int. Cl.
  *A61M 5/32* (2006.01)
  *G16H 20/13* (2018.01)
  *G16H 20/17* (2018.01)

(52) U.S. Cl.
  CPC ............. *G16H 20/13* (2018.01); *G16H 20/17* (2018.01); *A61M 2205/18* (2013.01); *A61M 2205/3306* (2013.01); *A61M 2205/3317* (2013.01); *A61M 2205/3584* (2013.01); *A61M 2205/505* (2013.01); *A61M 2205/52* (2013.01); *A61M 2205/581* (2013.01); *A61M 2205/583* (2013.01); *A61M 2205/587* (2013.01); *A61M 2205/6072* (2013.01); *A61M 2205/6081* (2013.01)

(58) Field of Classification Search
  CPC .. A61M 2205/3306; A61M 2205/3317; A61M 2205/3584; A61M 2205/505; A61M 2205/52; A61M 2205/581; A61M 2205/583; A61M 2205/587; A61M 2205/6072; A61M 2205/6081; G16H 20/17; G16H 20/13
  See application file for complete search history.

(56) References Cited

U.S. PATENT DOCUMENTS

| | | | |
|---|---|---|---|
| 2002/0175903 A1 | 11/2002 | Fahraeus et al. | |
| 2008/0125701 A1 | 5/2008 | Moberg et al. | |
| 2011/0306927 A1* | 12/2011 | Watanabe | A61M 5/5086 604/67 |
| 2014/0207080 A1 | 7/2014 | Allerdings | |
| 2014/0243750 A1 | 8/2014 | Larsen et al. | |
| 2016/0213853 A1* | 7/2016 | Despa | A61M 5/31548 |

| | | | |
|---|---|---|---|
| 2016/0220180 A1 | 8/2016 | Fateh | |
| 2017/0098058 A1* | 4/2017 | McCullough | G16H 20/17 |
| 2017/0332969 A1 | 11/2017 | Martin et al. | |
| 2018/0200451 A1* | 7/2018 | Shekalim | A61M 5/31525 |
| 2020/0289740 A1 | 9/2020 | Tamtoro et al. | |
| 2020/0345944 A1 | 11/2020 | Helmer | |

FOREIGN PATENT DOCUMENTS

| | | |
|---|---|---|
| CN | 105120925 | 12/2015 |
| CN | 106456884 | 2/2017 |
| EP | 2767297 | 8/2014 |
| EP | 2926846 | 10/2015 |
| EP | 2982400 | 2/2016 |
| JP | H11-513586 A | 11/1999 |
| JP | 2004-313672 | 11/2004 |
| JP | 2013020190 A | 1/2013 |
| JP | 2013-532019 A | 8/2013 |
| JP | 2016-514554 A | 5/2016 |
| WO | WO 2014/111340 | 7/2014 |
| WO | WO 2014/161953 | 10/2014 |
| WO | WO 2015/136513 | 9/2015 |
| WO | 2016086273 A1 | 6/2016 |
| WO | 2016203058 A1 | 12/2016 |
| WO | WO 2017/009724 | 1/2017 |
| WO | WO 2017/050781 | 3/2017 |
| WO | WO 2017/089502 | 6/2017 |

OTHER PUBLICATIONS

International Search Report and Written Opinion in International Appln. No. PCT/EP2018/086100, dated Mar. 8, 2019, 12 pages.
Communication pursuant to Article 94(3) EPC issued in European Patent Application No. 18816103.8 dated Oct. 31, 2025 (6 pages).
Notice of Reasons for Refusal for Japanese Patent Application No. 2024-230155 dated Sep. 7, 2025 (5 total pages, 2 in English).

* cited by examiner

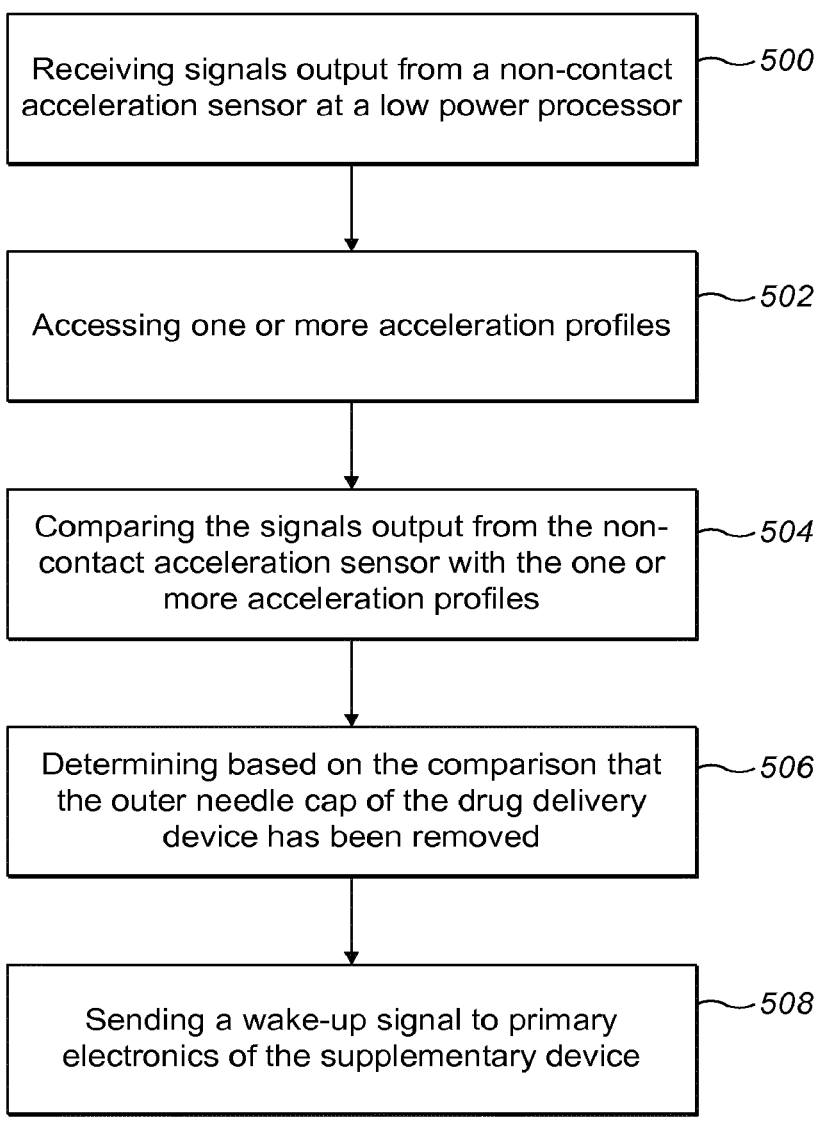

Receiving signals output from a non-contact acceleration sensor at a low power processor ~500

Accessing one or more acceleration profiles ~502

Comparing the signals output from the non-contact acceleration sensor with the one or more acceleration profiles ~504

Determining based on the comparison that the outer needle cap of the drug delivery device has been removed ~506

Sending a wake-up signal to primary electronics of the supplementary device ~508

FIG. 5

SENSOR DEVICE FOR ATTACHMENT TO AN INJECTION DEVICE

CROSS-REFERENCE TO RELATED APPLICATIONS

The present application is a continuation of U.S. patent application Ser. No. 16/957,330, filed on Jun. 23, 2020, which is the national stage entry of International Patent Application No. PCT/EP2018/086100, filed on Dec. 20, 2018, and claims priority to Application No. EP 17306950.1, filed on Dec. 28, 2017, the disclosures of which are incorporated herein by reference.

TECHNICAL FILED

The present disclosure relates to a device configured to retain a medicament delivery device, including an injection device, a syringe or a cartridge, to detect a user gesture and to wake up the device from a low power mode when the user gesture is detected.

BACKGROUND

A variety of diseases exists that require regular treatment by injection of a medicament. Such injection can be performed by using injection devices, which are applied either by medical personnel or by patients themselves.

Injection devices (i.e. devices capable of delivering medicaments from a medication container) typically fall into two categories—manual devices and injection devices. In a manual device—the user must provide the mechanical energy to drive the fluid through the needle. This is typically done by some form of button/plunger that has to be continuously pressed by the user during the injection.

Injection device devices aim to make self-administration of injected therapies easier for patients. Current therapies delivered by means of self-administered injections include drugs for diabetes (both insulin and newer GLP-1 class drugs), migraine, allergies, hormone therapies, anticoagulants etc. Injection device devices can be used to deliver a single dose of a particular life-saving drug. For example they are often prescribed to people who are at risk for anaphylaxis. They are also often used in the military to protect personnel from chemical warfare agents. Alternatively, injection devices are used to administer medicaments according to a prescribed therapeutic schedule for people suffering from Multiple Sclerosis, Rheumatroid Arthritis, Anemia, e.g.

Injection devices are devices which completely or partially replace activities involved in parenteral drug delivery from standard syringes. These activities may include insertion of a needle into a patient's skin, injection of the medicament, removal of the needle, shielding of the needle and preventing reuse of the device. This overcomes many of the disadvantages of manual devices. Forces required of the user, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Injection devices may be disposable or single use devices which may only be used to deliver one dose of medicament and which have to be disposed of after use. Other types of injection devices may be reusable. Usually they are arranged to allow a user to load and unload a standard syringe. The reusable injection device may be used to perform multiple parenteral drug deliveries, whereas the syringe is disposed after having been spent and unloaded from the injection device. The syringe may be packaged with additional parts to provide additional functionality. In a typical scenario a disease can be treated by patients themselves by injection of medicament doses using an injection device, for example on a daily, weekly, bi-weekly, or monthly basis.

Re-usable add-on devices suitable for use with injectors and which monitor the dose delivered by the injectors (and provide other information to a user) are known. Methods for minimizing the power consumption of such add-on devices are required.

SUMMARY

According to a first aspect of the disclosure, there is provided a supplementary device configured to be releasably attached to a distal end of a drug delivery device, the supplementary device comprising: primary electronics; a non-contact acceleration sensor located on or within the supplementary device, the non-contact acceleration sensor being directed towards a proximal end of the drug delivery device; and a low power processor configured to: receive the signals output from the non-contact acceleration sensor; determine based on the signals that an outer needle cap of the drug delivery device has been removed; in response to determining that an outer needle cap of the drug delivery device has been removed, send a wake-up signal to the primary electronics of the supplementary device.

In some embodiments, the supplementary device further comprises a memory readable by the low power processor, the memory storing one or more acceleration profiles.

In some embodiments, the memory storing software for comparing the signals output from the non-contact acceleration sensor with the one or more acceleration profiles.

In some embodiments, the supplementary device is configured to operate in a machine learning mode in which the one or more acceleration profiles are updated based on signals output from the non-contact acceleration sensor.

In some embodiments, each of the one or more acceleration profiles relates to a different type of drug delivery device.

In some embodiments, a first of the one or more acceleration profiles comprises data indicating rapid acceleration in a proximal direction followed by rapid deceleration in a proximal direction.

In some embodiments, the first of the one or more acceleration profiles further comprises data indicating approximately constant velocity between the rapid acceleration in the proximal direction and the rapid deceleration in the proximal direction.

In some embodiments, the first of the one or more acceleration profiles further comprises data indicating that the rapid deceleration in the proximal direction continues until the total change in velocity indicates movement in a distal direction.

In some embodiments, a second of the one or more acceleration profiles comprises data indicating rapid acceleration in a proximal direction followed by a sudden stop.

In some embodiments, the non-contact acceleration sensor is positioned so as to detect movement of a user's hand as it removes the outer needle cap.

In some embodiments, the supplementary device further comprises a position sensor located on or within the supplementary device, the position sensor being directed towards a proximal end of the drug delivery device and being configured to output signals indicative of the position and/or orientation of the user's hand and/or drug delivery device.

In some embodiments, the non-contact acceleration sensor is an electromagnetic reflection sensor.

In some embodiments, the non-contact acceleration sensor is an optical or infrared sensor.

In some embodiments, the position sensor is a passive infrared sensor or an accelerometer.

In some embodiments, the supplementary device further comprises a locking sensor configured to output signals indicative of whether the supplementary device is secured to the drug delivery device or not.

In some embodiments, the supplementary device further comprises a wireless unit configured to transmit data to one or more external devices.

In some embodiments, the supplementary device further comprises an electronic display configured to vary its display of information depending upon the signal output by the position and/or orientation sensor.

According to a second aspect of the disclosure, there is provided a method of operating a supplementary device configured to be releasably attached to a distal end of a drug delivery device, the method comprising: providing a non-contact acceleration sensor located on or within the supplementary device and being directed towards a proximal end of the drug delivery device to output signals; receiving the signals output from the non-contact acceleration sensor at a low power processor; the low power processor determining based on the signals that an outer needle cap of the drug delivery device has been removed; and in response to determining that the that an outer needle cap of the drug delivery device has been removed, sending a wake-up signal to primary electronics of the supplementary device.

In some embodiments, the method further comprising the low power processor: accessing one or more acceleration profiles; comparing the signals output from the non-contact acceleration sensor with the one or more acceleration profiles; and determining based on the comparison whether the outer needle cap of the drug delivery device has been removed.

According to a third aspect, there is provided a system comprising the supplementary device of any of claims 1 to 16 and the drug delivery device.

BRIEF DESCRIPTION OF THE FIGURES

FIG. 5 is a flowchart describing exemplary operation of FIGS. 2a, 2b, 3 and 4.

DETAILED DESCRIPTION

Figures 1A, 1B:
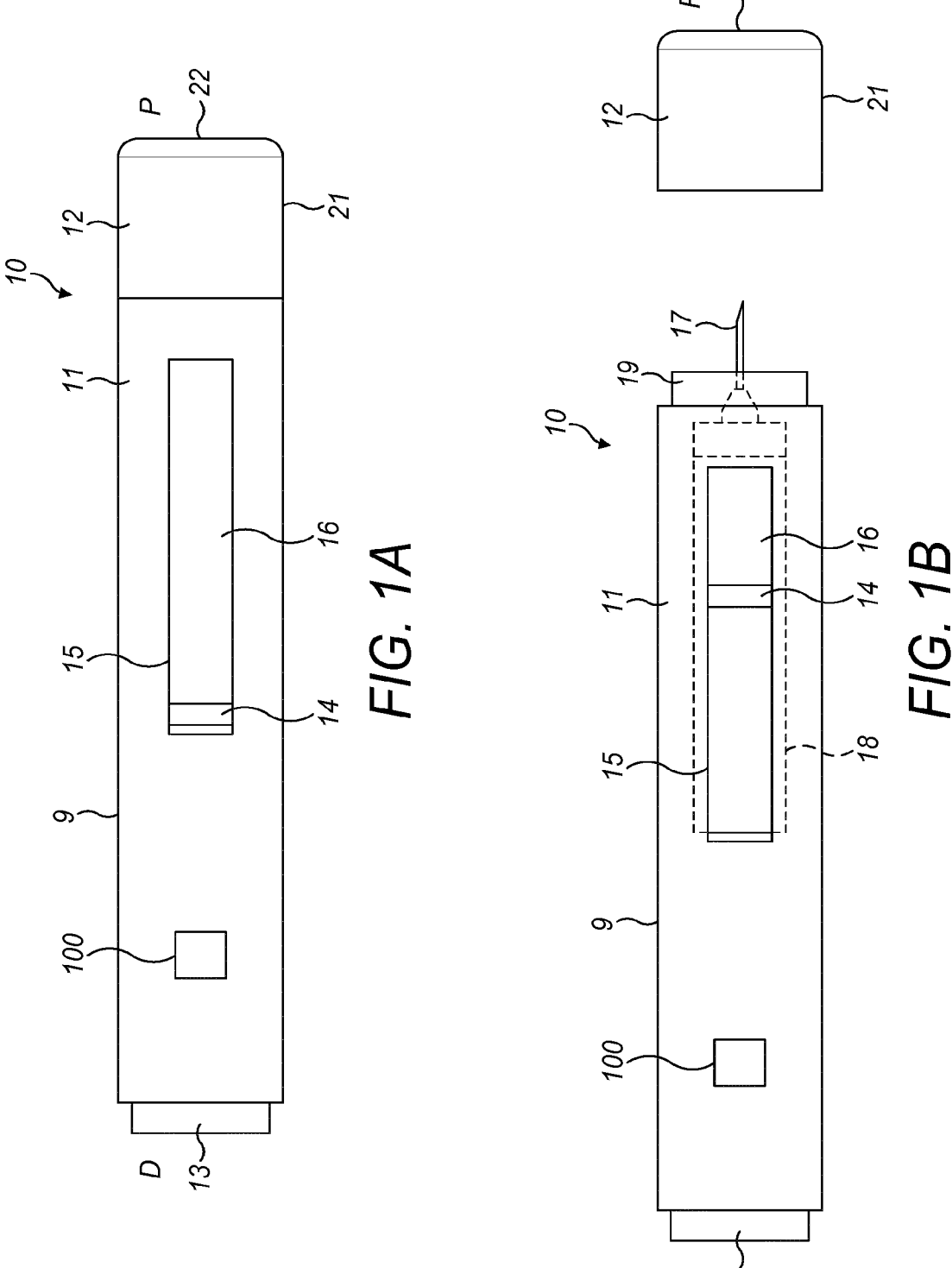
FIG. 1A shows a side view of an injection device.
FIG. 1B shows a side view of the injection device of FIG. 1A with a cap detached.

In the following, embodiments of the present disclosure will be described with reference to a pen injector. The present disclosure is however not limited to such applications and may equally well be deployed with other types of drug delivery devices, such as syringes, pre-filled syringes, needleless injectors and inhalers.

An injection device 10 (also referred to herein as a drug delivery device 10) according to embodiments will now be described with reference to FIGS. 1A and 1B. In some embodiments, the injection device 10 is a single use injection device 10, also known as auto-injectors. In some other embodiments, the injection device 10 is a re-usable injection device or an injection device which can be used to inject a number of doses before being discarded. The injection device 10 has a proximal end P and a distal end D. The proximal end P is directed towards the injection site of a patient during an injection while the distal end D is directed away from the injection site.

The injection device 10 comprises a body 9 and a cap 12 (also referred to herein as the outer needle cap 12 or ONC 12). The body 9 comprises an outer housing 11. The outer housing 11 is an elongate tube. The outer housing 11 includes a cartridge holder or syringe holder (not shown) which supports a cartridge or syringe 18 containing liquid medicament 16. Hereafter the description shall refer to a cartridge 18, which is supported by a cartridge holder (not shown). The cartridge 18 is shown in broken lines in FIG. 1B.

The outer housing 11 also houses a dispense mechanism (not shown) for causing dispensing of the medicament 16 during injection.

A hollow needle 17 communicates with an interior volume of the cartridge or syringe 18 and serves as a conduit for liquid medicament 16 during injection. The needle 17 and the cartridge 18 are in a fixed position relative to each other and to the body 9. A stopper, plunger, piston or bung 14 is moveable within the cartridge 18 to as to expel medicament contained within the cartridge 18 through the needle 17 under action of the dispense mechanism.

The dispense mechanism is mechanically coupled to the piston 14 of cartridge 18. The dispense mechanism is configured to move the piston axially along the cartridge 18 in a proximal direction to dispense medicament 16 through the needle 17. The dispense mechanism includes components that cooperate to apply a force to the piston 14 in response to an actuation input provided by a user. Here, the actuation input that triggers application of a force to the piston 14 is received by way of a dose dispense button 13 that is located at the distal end of the injection device 10. The dispense mechanism is mechanically coupled to the dispense button 13.

The body 9 also comprises a cap support 19 at the proximal end of the outer housing 11. The cap support is concentric with the outer housing 11 and may have a smaller diameter. The cap support 19 extends from the proximal end of the housing 11. The ONC 12 is received over the cap support 19 to close the proximal end of the body 9 and to cover the needle 17. The ONC 12 comprises a cylindrical wall 21 and an end wall 22. With the ONC 12 located on the body 9, as shown in FIG. 1A, an internal surface of the cylindrical wall 21 abuts an external surface of the cap support 19 in tightly abutting relation so that the ONC 12 is retained thereon in an attached position. The ONC 12 may therefore be retained on the cap support by frictional abutment.

The cap support 19 may comprise one or more protrusions on its outer surface, for example one or more annular flanges. The ONC 12 may comprise one or more corresponding indentations on its inner surface, for example an annular indentation. These features may connect or co-operate when the ONC 12 is attached to the injection device 10 to increase the frictional force holding the ONC 12 onto the injection device 10 and consequently to increase the force required to remove the ONC 12 from the injection device 10.

To inject the medicament 16, the ONC 12 is removed from the device 10 by the user, resulting in the arrangement shown in FIG. 1B. Next, the proximal end of the injection device 10 is placed against an injection site of a patient, which may be the user or another person. The user then actuates the dispense button 13. This causes the dispense mechanism to force the piston 14 to expel medicament from the cartridge 18 through the needle 17 into the injection site of the patient.

Some other injection devices (not shown) may comprise an actuation sleeve in the form of an elongated cap support 19 which extends beyond the point of the needle 17 before the injection device is activated. Here, the actuation input that triggers application of a force to the piston 14 is received by movement of the actuation sleeve in a distal direction, which is configured to trigger operation of the injection device. The ONC 12 is received over the actuation sleeve to close the proximal end of the body 9. Such injection devices may have no dispense button.

After a user injects a quantity of medicament into their skin, it is advantageous for the needle to be left in position for a short time (e.g. 5-20 seconds). This allows the medicament to be diffused away from the injection site by action of the user's blood flow. This is often referred to as "dwell time". If the needle is removed too soon after an injection, it can result in medicament being expressed from the injection site and the user therefore not receiving a full dose.

The cartridge 18 is transparent and a window 15 is provided in the housing 11 coincident with the cartridge 18 so that the medicament 16 contained within the cartridge 18 is visible. A user of the injection device this is able by inspection to determine whether the entire quantity of medicament 16 has been ejected from the cartridge 18 during the injection.

A label is provided on the housing 11. The label includes information 100 about the medicament included within the injection device 10, including information identifying the medicament. The information 100 identifying the medicament may be in the form of text. The information 100 identifying the medicament may also be in the form of a colour. The information 100 identifying the medicament may also be encoded into a barcode, QR code or the like. The information 100 identifying the medicament may also be in the form of a black and white pattern, a colour pattern or shading.

Figure 2A:
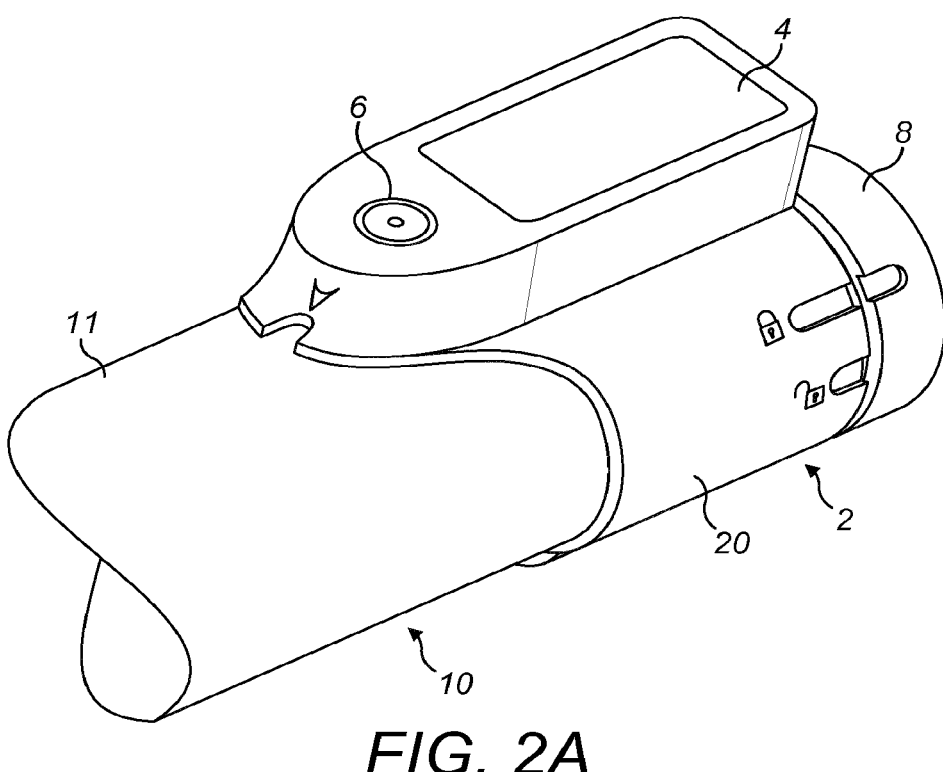
FIGS. 2a and 2b show a perspective view of a supplementary device releasably attached to the injection device of FIGS. 1a and 1b.

FIG. 2a is a schematic illustration of an embodiment of a supplementary device 2 releasably attached to injection device 10 of FIG. 1. The supplementary device 2 is suitable for use with the injection device shown in FIGS. 1A and 1B and other types of injection device as discussed above. Supplementary device 2 comprises a housing configured to encircle the housing 11 of injection device 10 of FIG. 1, so that the injection device 10 is at least partially retained within the supplementary device 2, but is nevertheless removable from the supplementary device 2, for instance when injection device 10 is empty and has to be replaced. The injection device 10 and supplementary device 2 may optionally comprise co-operating alignment features to ensure that the supplementary device 2 is correctly orientated and positioned with respect to the injection device 10.

Figure 2B:
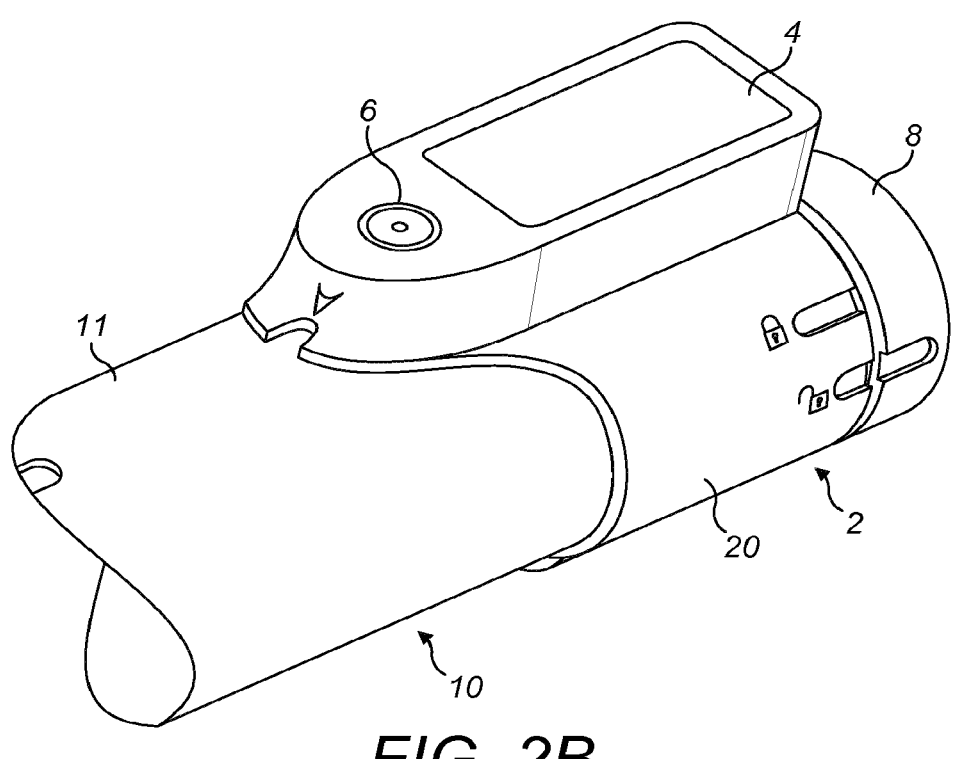

The supplementary device 2 has an attachment mechanism 8 for securing and un-securing the supplementary device 2 with the injection device 10. The attachment mechanism 8 may be rotatable relative to the main body 20 of the supplementary device 2 between a locked and an unlocked position. FIG. 2a shows the attachment mechanism 8 in a locked position. FIG. 2b shows the attachment mechanism 8 in an unlocked position. In some other embodiments, the supplementary device 2 may be secured to the injection device 10 by a simple friction fit.

Information is displayed via display unit 4 of supplementary device 2. The display unit 4 may be a colour LCD screen. The display unit may be a touch sensitive screen. For example, the 4 may indicate the time and date of the next scheduled injection for the user of the supplementary device 2. During operation of the injection device 10, the supplementary device 2 may also display information to assist the user, as will be described in greater detail below.

The supplementary device 2 may also comprise at least one user input 6 such as a touch sensitive button. The user input 6 may comprise one or more LEDs. These may form a ring around the button and/or illuminate the whole of the button. The user input 6 may allow a user to turn on/off supplementary device 2, to trigger actions (for instance to cause establishment of a connection to or a pairing with another device, and/or to trigger transmission of information from supplementary device 2 to another device), or to confirm something.

Figure 3:
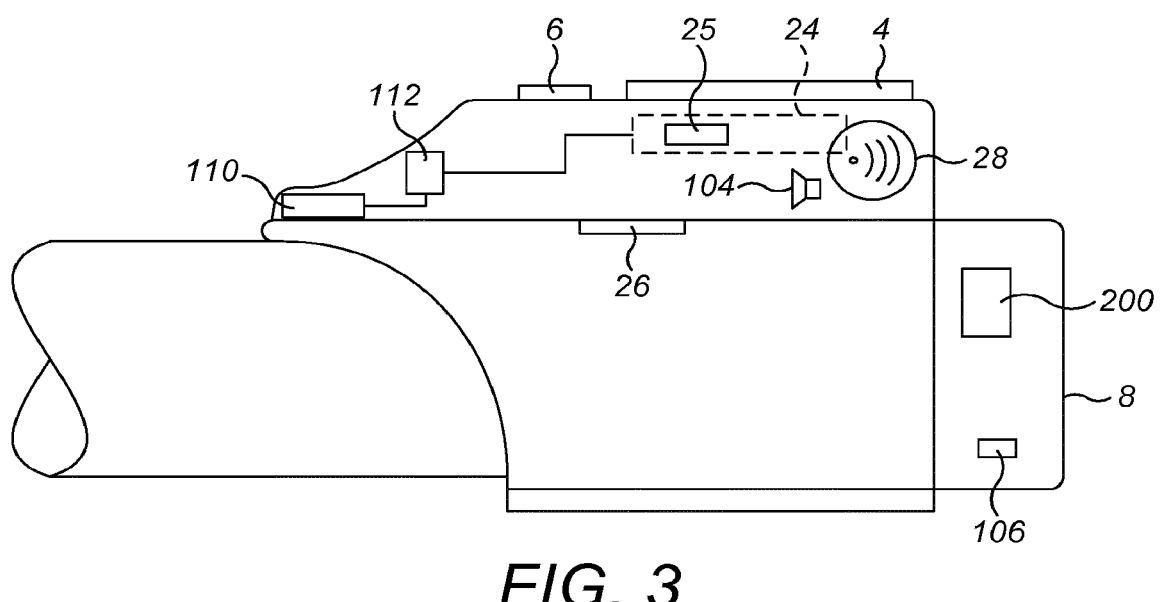
FIG. 3 shows a side view of the supplementary device of FIGS. 2a and 2b and an attached injection device and illustrates some of the major internal and external components of the supplementary device.

FIG. 3 illustrates some of the major internal and external components of the supplementary device 2 in a state where it is attached to injection device 10 shown in FIGS. 1A and 1B. Externally, the supplementary device 2 comprises the display unit 4, the user input 6, attachment mechanism 8 and a battery compartment 102.

Internally, the supplementary device 2 comprises primary electronics 24. The primary electronics 24 comprise at least a processor 25 and memory. The primary electronics 24 may comprise both a program memory and a main memory. The processor 25 may for instance be a microprocessor, a Digital Signal Processor (DSP), Application Specific Integrated Circuit (ASIC), Field Programmable Gate Array (FPGA) or the like. The processor 25 executes program code (e.g. software or firmware) stored in the program memory, and uses a main memory, for instance to store intermediate results.

The main memory may also be used to store a logbook on performed ejections/injections. The program memory may for instance be a Read-Only Memory (ROM), and the main memory may for instance be a Random Access Memory (RAM).

The supplementary device 2 also comprises a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form. The transmitted data also includes a time stamp associated with an injection.

The supplementary device 2 also comprises an audio module 104 configured to provide audio feedback to a user of the supplementary device 2. Both the wireless unit 28 and audio module 104 may be coupled to and controlled by the primary electronics 24. The supplementary device 2 may optionally comprise a locking sensor 106 configured to sense whether the attachment mechanism is in the locked position or the unlocked position.

The supplementary device 2 may also comprise an optical sensor 26 for reading the information 100 identifying the medicament. The information 100 identifying the medicament may be the colour of the housing 11 of the injection device, or the colour of an area of the housing or a label affixed to the housing. In these embodiments, the optical sensor 26 may be a simple photometer configured to detect the colour. In some other embodiments, the information 100 identifying the medicament may be a QR code, or other similar encoded information and the optical sensor 26 may be a camera or QR code reader. Further, one or more light sources may be provided to improve reading of optical sensor 26. The light source may provide light of a certain wavelength or spectrum to improve colour detection by optical sensor 26. The light source may be arranged in such a way that unwanted reflections, for example due to the curvature of the housing 11, are avoided or reduced. In an example embodiment, the optical sensor 26 is a camera unit configured to detect a code 100 (for instance a bar code, which may for instance be a one- or two-dimensional bar code) related to the injection device and/or the medicament contained therein. This code 100 may for instance be located on the housing 11 or on a medicament container contained in injection device 10, to name but a few examples. This code 100 may for instance indicate a type of the injection device and/or the medicament, and/or further properties (for instance an expiration date). This code 100 may be a QR code 100. The QR code is in general black and white and thus no colour detection is required on the part of the optical sensor 26. This allows the optical sensor 26 to be simple and cheap to manufacture.

The processor 25 may be configured to check the information 100 read by the optical sensor 26 against pre-stored information in order to verify that the user is injecting the correct medicament. If the processor 25 does not recognise the information 100 or recognises the information 100 as indicating a different medicament to that which the user should be receiving at that time, then the supplementary device 2 may produce an alarm signal. The alarm signal may comprise words or graphics displayed on the display unit 4 or sound produced by the audio module 104. Alternatively, or in addition, the supplementary device 2 may send an alarm signal to an external device via wireless unit 28.

The supplementary device 2 comprises a non-contact acceleration sensor 110 (also referred to herein as a non-contact sensor or first non-contact sensor). The non-contact acceleration sensor 110 is located on or within the supplementary device and is directed towards a proximal end of the drug delivery device. For example, the non-contact acceleration sensor 110 may be disposed on the surface of the supplementary device 2 or may be retained within the supplementary device 2. Depending on the sensor technology used, a transparent window may cover the non-contact acceleration sensor 110 to prevent contamination and damage.

The non-contact acceleration sensor 110 is configured to output signals indicative of the change in velocity of a user's hand relative to the sensor 110 as the user removes the ONC 12 from the injection device 10. The non-contact acceleration sensor 110 may be referred to as a non-contact sensor, since it is able to sense the change in velocity of a user's hand without contact between the sensor 110 and the user's hand.

The non-contact acceleration sensor 110 sensor may be positioned such that it does not or cannot detect movement of the ONC 12 itself.

The supplementary device 2 also comprises a low power processor 112. The non-contact acceleration sensor 110 is in communication with the low power processor 112 and may be at least partially controlled by the low power processor 112. Both the low power processor 112 and the non-contact acceleration sensor 110 may draw power from a battery (not shown) and are designed to draw only a very small current so that the supplementary device operates in a low power mode.

The supplementary device 2 may also comprise a memory (not shown) storing one or more acceleration profiles. The one or more acceleration profiles represent typical movement of a user's hand when removing the ONC 12. In some embodiments this memory is a separate component, while in other embodiments this memory is integral with the low power processor 112 or integral with the non-contact acceleration sensor 110. In other words, the low power processor 112 may be preprogramed with at least one acceleration profile or may have access to at least one acceleration profile indicative of typical cap removal movement.

The low power processor 112 is connected to the primary electronics 24 and is configured to exchange signals with the processor 25 of the primary electronics 24. The low power processor 112 is configured to receive the signals output by the non-contact acceleration sensor 110 and to determine the change in velocity of the user's hand relative to the non-contact acceleration sensor 110. The low power processor 112 is configured to determine whether the received signals are indicative of a typical cap removal movement of the user's hand. The low power processor 112 may do this by checking the received signals against the one or more acceleration profiles. When the low power processor 112 determines that the received signals are indicative of a typical cap removal movement of the user's hand, it sends a wake-up signal to the primary electronics 24.

A typical hand movement of a user when removing the ONC 12 involves the overcoming of the static friction force securing the ONC 12 to the injection device 10. This force may be increased by feature such as flanges, indentations and undercuts as previously described. The user therefore increases the pulling force on the ONC 12 until the friction force is overcome and the ONC is suddenly released from the injection device 10. This results in a rapid acceleration in the proximal direction which is detected by the non-contact acceleration sensor 110. It takes some moments for the user to react to the release of the ONC 12. When the user reacts they quickly reduce the force applied to the ONC 12 resulting in a rapid deceleration (in the proximal direction) which is detected by the non-contact acceleration sensor 110. There may be a period of approximately constant velocity (or more moderate acceleration or deceleration) between the rapid proximal acceleration and rapid proximal deceleration. A first acceleration profile may represent the ONC cap removal process described above and be stored in the memory as previously described.

In some cases, when the user reacts to the sudden acceleration caused by release of the friction connection, they cause the ONC 12 to move back towards the injection device a small distance, i.e. in an approximately distal direction, before bringing the ONC 12 to a stop. In other words, the rapid deceleration in the proximal direction continues until the total change in velocity indicates a change of direction from proximal to distal, before the ONC 12 again brought to a stop. A second acceleration profile may represent this change of direction ONC cap removal process.

Some users may remove the ONC 12 is a different way. For example, the may remove the ONC 12 less carefully. This may result in a rapid acceleration as the friction force holding the ONC 12 and the rubber needle shield of the syringe to the injection device is overcome, followed by a period of approximately constant velocity (or more moderate acceleration) until the user's hand is moved out of the range or viewing angle of the non-contact acceleration sensor 110. In other words, there is a characteristic rapid acceleration followed by an abrupt stop (due to the user's hand moving out of range of the sensor 110). The abrupt stop may be indicated by a termination of signals received by the processor 112 from the non-contact acceleration sensor (i.e. a loss of signal from the acceleration sensor may be indicative of an abrupt or sudden stop). A third acceleration profile may represent this less careful ONC cap removal process.

Numerous variants of the acceleration profiles described above may also be stored in the memory to account for variation in static friction force between the ONC 12 and injection device 10, and variations in the way a user performs each individual cap removal process.

The low power processor 112 sends a wake-up signal to the primary electronics 24 only when it determines that the ONC 12 has been removed. This has the advantage of minimizing the power consumption of the supplementary device 2, since the low power processor 112 and non-contact acceleration sensor 110 are configured to draw less power than the primary electronics.

Figure 4:
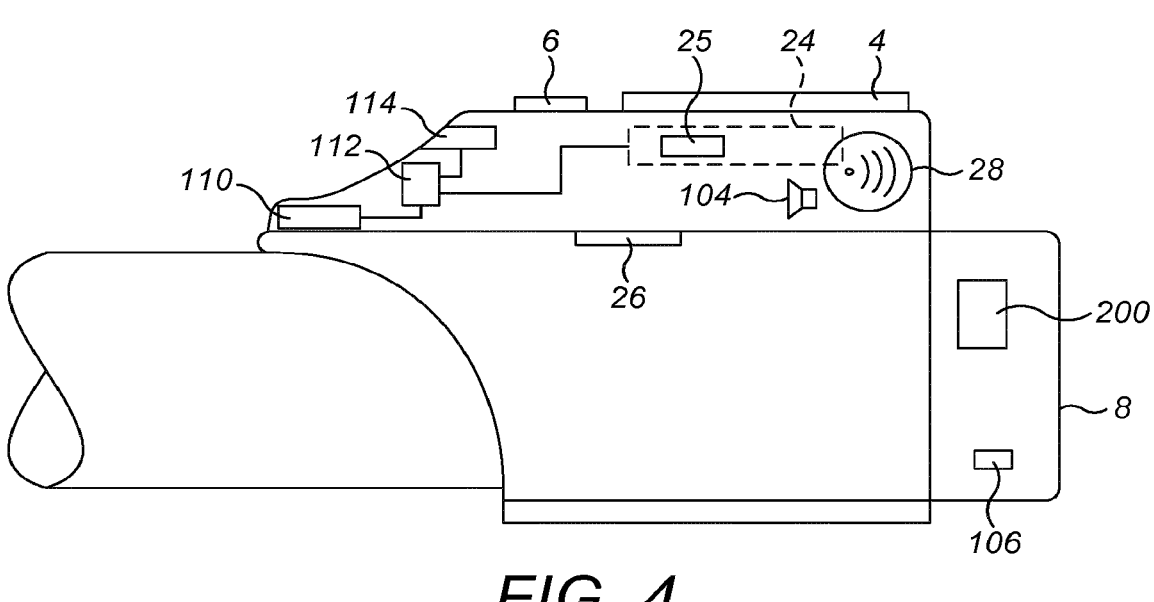
FIG. 4 shows a side view of the supplementary device of FIGS. 2a and 2b according to further embodiments and an attached injection device.

FIG. 4 illustrates an alternative supplementary device 2 according to further embodiments. In addition to the components already described with respect to FIG. 3, the supplementary device 2 of FIG. 4 comprises a position sensor 114. The position sensor 114 may be connected to and at least partially controlled by the low power processor 112. The position sensor 114 is located on or within the supplementary device and is directed towards a proximal end of the drug delivery device. The position sensor 114 is configured to output signals indicative of the position and/or orientation of the user's hand. For example, it may be possible to determine from the signals output by the position sensor 114, whether the user is using their left hand or right hand to grasp the ONC 12. The memory may store separate acceleration profiles for left and right hand removal of the ONC 12 and the signals from the position sensor 114 may therefore be used to inform the low power processor 112 of which acceleration profiles to check. In some embodiments, the memory may store separate orientation profiles associated with particular orientations of the ONC when it is being grasped by the left or right hand of the user. Thus, the position sensor 114 may be a passive infrared sensor, a capacitive displacement sensor or an electronic three-axis sensor (e.g. a three-axis accelerometer or three-axis compass). The position sensor 114 may comprise one or more of these types of sensor.

After the low power processor 112 has determined whether the user is using their left hand or right hand to grasp the ONC 12, it may use this information to control the orientation of the information displayed in the display 4. For example, if the ONC 12 is being grasped by the left hand of the user, then the low power processor 112 may send a signal to the display 4 prompting it to display information to the user in a format such that it can be easily be read by the user in this (i.e. "left handed") orientation. If, however, the injection device 10 is being grasped by the right hand of the user, then the low power processor 112 may send a signal to the display 4 prompting it to display information in a format such that it can be easily read by the user in this (i.e. "right handed") orientation. This improves the ease of use of the device by improving the readability of the display.

In some embodiments, the position sensor 114 can be configured to determine the orientation of the supplementary device 10 and thus the orientation of the injection device 10. When the user grasps the injection device 10 in order to remove the ONC 12, the injection device 10 will typically be held by the user in a particular orientation. The position sensor 114 may be configured to detect the orientation and send a signal to the low power processor 112. Similarly, when the injection device is used (i.e. to perform an injection), the injection device is held in a particular orientation by the user. The position sensor 114 may be configured to detect this orientation and send a signal to the low power processor 112.

The low power processor 112 is configured to receive the signals output by the non-contact acceleration sensor 110 and to determine the orientation of the injection device. The low power processor 112 is configured to determine whether the received signals are indicative that the pen is in an orientation whereby the cap is to be removed by the user, or whereby an injection is about to be commenced. The low power processor 112 may do this by checking the received signals against the one or more orientation profiles. When the low power processor 112 determines that the received signals are indicative of a typical orientation, it sends a wake-up signal to the primary electronics 24. If the low power processor 112 determines that the received signals are indicative that the injection device 10 is not in a typical orientation (e.g. if it does not correlate with a particular profile), then the low power processor 112 may not send a wake-up signal to the primary electronics 24, or it may send a signal which indicates that the injection device 10 is not in a typical orientation.

The non-contact acceleration sensor 110 may take a number of different forms. For example, an electromagnetic sensor which operates based on electromagnetic reflection. The sensor 110 may use optical or infra-red light and rely on the Doppler shift of the light reflected form the moving hand of the user to detect the acceleration. Alternatively, microwaves or radio waves may be used. These have the advantage of being intrinsically lower in energy than visible light, and may pass through an opaque section of the housing 20 of the supplementary device 2. Alternatively, the non-contact acceleration sensor 110 may be embodied as a capacitive displacement sensor. The proximity of the user's hand changes the capacitance detected by the sensor. In some other embodiments a capacitive displacement sensor may be used as a combined non-contact acceleration sensor 110 and absolute position sensor 114.

The supplementary device 2 may also be placing into a machine learning mode in which the acceleration profiles can be created or updated. For example a user or technician may use the touch screen 4 to enter a non-contact acceleration sensor learning mode. The user or technician may then repeatedly remove and replace the ONC 12 of the injection device 10 under instruction from the display 4 of the supplementary device 2. In this way, the supplementary device 2 can refine the acceleration profile to better match the real world situation, or create new acceleration profiles which better match the way in which a particular user removes the ONC 12.

The supplementary device 2 may comprise a number of other components and perform a number of other functions. For example the housing 20 of the supplementary device 2 may retain at least one further non-contact sensor (not shown) arranged to lie adjacent to the outer housing 11 of the injection device 10 and to detect movement of one or more moveable components within the injection device. Movement of the moveable components may be associated with activation of the injection device and ejection of a medicament. Examples of moveable components are (i) a spring, for example a pre-compressed spring which uncompresses during medicament ejection, (ii) an element configured to move between two different configurations depending on whether the injection device is in a pre-activation state or a post-activation state, (iii) a slidable element which moves longitudinally, for example form the distal to the proximal end of the injection device 10, during medication ejection, or (iv) a rotatable sleeve configured to rotate during medication ejection.

The primary electronics 24 may receive the signals from the at least one further non-contact sensor and infer an operational state of the injection device 10 and cause information regarding the timing of the operation of the injection device 10 to be recorded in the main memory and/or transmitted to an external device via the wireless unit 28. The primary electronics may also cause information regarding the operational state of the injection device 10 to be displayed on the display 4 of the supplementary device 2. For example, the display 4 may indicate whether the injection device is in a pre-activation state, a currently injecting state, a holding (or "dwell time") state or a post-activation state.

FIG. 5 shows a flow chart illustrating operations which can be performed by the supplementary device 2.

At step 500, the low power processor 112 receives signals from the non-contact acceleration sensor 110. At step 502 one or more acceleration profiles are accessed. As previously described the low power processor 112 or the non-contact acceleration sensor 110 may be pre-programmed with the acceleration profiles. Alternatively, the low power processor 112 may access a memory to retrieve the acceleration profiles. At step 504 the signals output from the non-contact acceleration sensor are compared with the one or more acceleration profiles to determine a match. The match does not necessarily need to be exact, and tolerances for the different sections of each acceleration profile may be set. At step 506, the low power processor 112 determines based on the comparison that the outer needle cap of the drug delivery device has been removed.

Steps 500 to 506 may be a constant and ongoing process whenever the supplementary device 2 is attached to an injection device 10, for example whenever the locking sensor 106 indicates that the attachment mechanism 8 has been locked. Once the low power processor 112 has determined that the outer needle cap of the drug delivery device has been removed, at step 508 it sends a wake-up signal to the primary electronics 24 of the supplementary device. The primary electronics 24 may then perform their functions of monitoring the movement of components with in the injection device 10 and determining and displaying the status on the display 4.

In some embodiments, there may be further operation steps performed by the supplementary device 2. The low power processor 112 may, based upon the signals it receives from both the non-contact acceleration sensor 110 and the position sensor 114, determine whether the ONC 12 has been removed. For example, if the signals received from both the non-contact acceleration sensor 110 and the position sensor 114 indicate that the ONC 12 has been removed, then the low power processor 112 may determine that the ONC 12 has been removed and send a wake-up signal to the primary electronics 24 of the supplementary device. If, however, the low power processor 112 receives only one signal from either the non-contact acceleration sensor 110 or the position sensor 114, then the low power processor 112 may determine that the ONC 12 has not been removed and not send a wake-up signal to the primary electronics 24 of the supplementary device. These additional processing operations may form part of steps 506 and 508, or be a separate step or a series of steps.

By using both the signal received from the non-contact acceleration sensor 110 and the signal received from the position sensor 114 in this way (i.e. information received from two sources), a more accurate determination of whether the ONC 12 has been removed can be made, and thus reduce power consumption.

In some embodiments, after the low power processor 112 has determined that the ONC 12 of the drug delivery device has been removed, the low power processor 112 may start a timer (e.g. a countdown timer). If the low power processor 112 does not receive a signal from the components of the device which indicates that the actuation sleeve or piston 14 has been operated within the period set by the timer (e.g. 1 minute), then the low power processor 112 may send a signal to the display 4. This may occur when the user has removed the ONC 12 but not commenced the injection procedure. If this occurs, there is a risk that the needle will become clogged as it will be possible for medicament contained within the bore of the needle to come into contact with the air and, for example, dry out (i.e. by evaporation). Therefore, if the display 4 receives a signal indicative of this condition, then display 4 may display a warning status to remind the user that the ONC 12 has been removed and prompting the user to begin injection or replace the ONC 12, thereby reducing the amount of time that the ONC 12 is removed from the device and helping to prevent clogging of the needle. Alternatively or in addition, in some embodiments, the user may also be prompted to commence injection or replace the cap by an audible signal (e.g. the low power processor 112 may send a signal to a speaker or alarm).

In some embodiments, the timer period may be predefined and stored in the program memory of the supplementary device. Alternatively or in addition, the timer period may be modified by the user and stored in the main memory of the device, or created or updated using the machine learning mode and stored in the main memory.

The processor 112 may further be configured to use signals received from a sensor (not shown) that detects movement of the actuation sleeve or piston 14 which indicates that injection is taking place.

Figure 6:
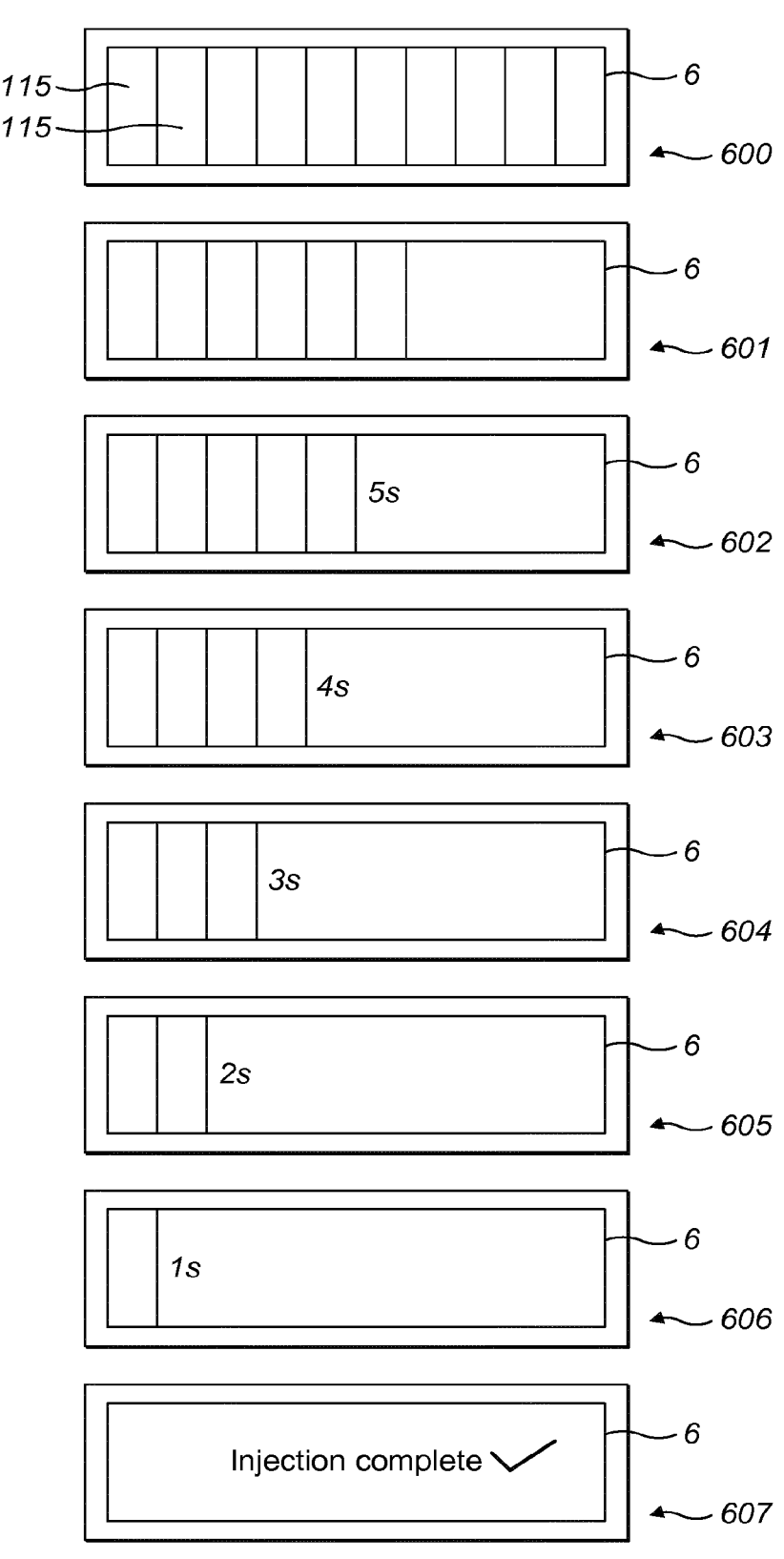
FIG. 6 depicts a display of the supplementary device when in use and shows various statuses of the device.

FIG. 6 depicts the display 4 of the device 2 illustrating eight different injector pen statuses (600-607). Status 600 may be displayed on the display 4 after removal of the ONC 12 is detected (as discussed above) and prior to injection commencing. As can be seen, the display 4 shows a number of segments, bars or blocks 115, which can be individually illuminated. The display could alternatively show other means of depicting a change in time, such as an analogue clock or a shaded area which changes size. Before starting the injection, the blocks 115 occupy the majority of the display 4, which illustrates that the medicament delivery device contains medicament and that injection has not yet commenced.

During injection, the amount of medicament contained in the device 2 decreases and this is detected by signals received by the processor 112 from the sensor that detects movement of the actuation sleeve or piston 14. This may be illustrated by changes in the number of blocks 115 occupying the display 4. For example, the number of blocks 115 decreases (as shown in status 601) during injection. In some embodiments, the display 4 starts with all of the blocks 115 illuminated, indicating that the medicament delivery device is unused. The blocks 115 are then removed sequentially from right to left until no blocks are displayed, indicating that the medicament delivery device is empty. The display may be dynamic during the injection process, e.g. the blocks 115 may flash on and off.

After a user injects a quantity of medicament into their skin, it is advantageous for the needle to be left in position for a short time (e.g. 5-20 seconds). This is known as the "dwell time" or "hold time". This allows the medicament to be diffused away from the injection site by action of the user's blood flow. If the needle is removed too soon after an injection, it can result in medicament being expressed from the injection site and the user therefore not receiving a full dose. As previously stated the processor 112 can use the change in signals received from the actuation sleeve or piston sensors to determine that an injection is being performed. The processor 112 can infer that the injection has been completed when the signals received from the sensors stop changing. This detection can therefore be used as a trigger to display an indication to the user on the display unit 4 instructing them to leave the needle of the injection device 10 in the injection site for a predetermined length of time. The indication may be of any suitable form, for example a timer which counts up or down or a graphic which gets larger/smaller or which fills or un-fills. As shown in statuses 602, 603, 604, 605 and 606, the indicator can countdown over a period of time. For example, the indicator may countdown over a period of 5 seconds. This may be illustrated by a reduction in the number of blocks 115 occupying the display. As shown in status 607, at the end of the dwell time, the display may change to inform the user that the injection is complete. The user may also be informed that the injection is complete by an audible signal. Other methods of indication may also be used (e.g. vibration).

In addition to the statuses shown in FIG. 6, the display may show other information to the user. For example, it may indicate to the user when to change the injection device (e.g. when it is empty).

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts. Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A supplementary device configured to be releasably attached to a distal end of a drug delivery device during an injection, the distal end being directed away from an injection site during the injection, the supplementary device comprising:

primary electronics;

a non-contact acceleration sensor located on or within the supplementary device; and a low power processor configured to:

operate in a lower power mode;

receive signals output from the non-contact acceleration sensor;

determine, based on the signals, an orientation of the drug delivery device; and determine, based on the determined orientation of the drug delivery device, whether to send a wake-up signal to the primary electronics, wherein the wake-up signal wakes up the supplementary device from the lower power mode so that the primary electronics are configured to operate in a higher power mode, wherein the supplementary device is configured such that, when it is attached to the distal end of the drug delivery device, it at least partially covers the distal end of the drug delivery device.

2. The supplementary device according to claim 1, wherein the signals output from the non-contact acceleration sensor are indicative of the orientation of the drug delivery device.

3. The supplementary device according to claim 1, wherein the low power processor is configured to compare the signals output from the non-contact acceleration sensor and received by the low power processor with one or more orientation profiles.

4. The supplementary device according to claim 3, wherein the low power processor is configured to determine whether the determined orientation of the drug delivery device is a typical orientation by comparing the determined orientation with the one or more orientation profiles.

5. The supplementary device according to claim 3, wherein the supplementary device further comprises a memory readable by the low power processor, the memory storing the one or more orientation profiles.

6. The supplementary device according to claim 5, the memory storing software for comparing the signals output from the non-contact acceleration sensor with the one or more orientation profiles.

7. The supplemental device according to claim 3, wherein the low power processor is configured to determine that the drug delivery device is not in a typical orientation if the received signals do not correspond with an orientation profile of the one or more orientation profiles.

8. The supplementary device according to claim 1, wherein the low power processor is configured to send the wake-up signal to the primary electronics if the determined orientation is a typical orientation.

9. The supplementary device according to claim 1, wherein the low power processor is configured to not send the wake-up signal to the primary electronics if the determined orientation is not a typical orientation.

10. The supplementary device according to claim 1, wherein the low power processor is configured to send a signal to the primary electronics indicating that an injection device is not in a typical orientation if the determined orientation is not a typical orientation.

11. The supplementary device according to claim 1, wherein the signals output from the non-contact acceleration sensor and received by the low power processor are indicative that the drug delivery device is in an orientation whereby a cap is to be removed.

12. The supplementary device according to claim 1, wherein the signals output from the non-contact acceleration sensor and received by the low power processor are indicative that the drug delivery device is in an orientation whereby an injection is about to be commenced.

13. The supplementary device according to claim 1, wherein the non-contact acceleration sensor is directed towards a proximal end of the drug delivery device.

14. The supplementary device according to claim 1, wherein the supplementary device is releasably attached to the distal end of the drug delivery device.

15. The supplementary device of claim 1, wherein the supplementary device is configured such that, when it is attached to the distal end of the drug delivery device, it fully covers the distal end of the drug delivery device.

16. The supplementary device of claim 1, wherein the supplementary device is configured such that, when it is attached to the distal end of the drug delivery device, it covers a button at the distal end of the drug delivery device.

17. The supplementary device of claim 1, wherein the supplementary device comprises a housing configured to receive and cover the distal end of the supplementary device.

18. A supplementary device configured to be releasably attached to a distal end of a drug delivery device during an injection, the distal end being directed away from an injection site during the injection, the supplementary device comprising:

primary electronics;

a non-contact acceleration sensor located on or within the supplementary device;

a position sensor located on or within the supplementary device; and a low power processor configured to:

operate in a lower power mode;

receive signals output from the non-contact acceleration sensor;

receive signals output from the position sensor;

determine based on the signals output by the non-contact acceleration sensor and the signals output by the position sensor whether an outer needle cap of the drug delivery device has been removed; and in response to determining that the outer needle cap of the drug delivery device has been removed, send a wake-up signal to the primary electronics of the supplementary device, wherein the wake-up signal wakes up the supplementary device from the lower power mode so that the primary electronics can operate in a higher power mode, wherein the supplementary device is configured such that, when it is attached to the distal end of the drug delivery device, it at least partially covers the distal end of the drug delivery device.

19. The supplementary device according to claim 18, wherein the low power processor is configured to determine that the outer needle cap of the drug delivery device has been removed if the signals received from the non-contact acceleration sensor and the signals output by the position sensor indicate that the outer needle cap has been removed.

20. The supplementary device according to claim 18, wherein the position sensor is configured to output signals indicative of the position and/or orientation of a user's hand and/or drug delivery device.

21. The supplementary device according to claim 18, wherein the position sensor and the non-contact acceleration sensor are directed towards a proximal end of the drug delivery device.

22. The supplementary device according to claim 18, wherein the position sensor is a passive infrared sensor or an accelerometer.

23. A supplementary device configured to be releasably attached to a distal end of a drug delivery device during an injection, the distal end being directed away from an injection site during the injection, the supplementary device comprising:

primary electronics;

a non-contact acceleration sensor located on or within the supplementary device, the non-contact acceleration sensor being directed towards a proximal end of the drug delivery device;

a low power processor configured to:

operate in a lower power mode;

receive signals output from the non-contact acceleration sensor, determine based on the signals that an outer needle cap of the drug delivery device has been removed, and in response to determining that the outer needle cap of the drug delivery device has been removed, send a wake-up signal to the primary electronics of the supplementary device, wherein the wake-up signal wakes up the supplementary device from the lower power mode so that the primary electronics can operate in a higher power mode; and a memory readable by the low power processor, the memory storing one or more acceleration profiles, wherein one or more acceleration profiles comprises data indicating acceleration in the proximal direction followed by a sudden stop, wherein the supplementary device is configured such that, when it is attached to the distal end of the drug delivery device, it at least partially covers the distal end of the drug delivery device.

* * * * *